(12) United States Patent
Bauer et al.

(10) Patent No.: US 11,483,991 B2
(45) Date of Patent: Nov. 1, 2022

(54) METHODS FOR GENOTYPING HAPLOID EMBRYOS

(71) Applicant: Monsanto Technology LLC, St. Louis, MO (US)

(72) Inventors: Christopher T. Bauer, University City, MO (US); David V. Butruille, Huxley, IA (US); Edward J. Cargill, Maryland Heights, MO (US); Daniel Challis, Huxley, IA (US); Fenggao Dong, Chesterfield, MO (US); Fengxing Du, Chesterfield, MO (US); Brian W. Gardunia, Huxley, IA (US); Yang Ju Im, Ellisville, MO (US); Jonathan C. Lamb, Wildwood, MO (US); Piyaraj Nan Newton, St. Louis, MO (US); Pierre Sehabiague, Larressore (FR); Ruth A. Wagner, Chesterfield, MO (US); Shengqiang Zhong, Creve Coeur, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

(21) Appl. No.: 17/049,957

(22) PCT Filed: Apr. 25, 2019

(86) PCT No.: PCT/US2019/029204
§ 371 (c)(1),
(2) Date: Oct. 22, 2020

(87) PCT Pub. No.: WO2019/210100
PCT Pub. Date: Oct. 31, 2019

(65) Prior Publication Data
US 2021/0235644 A1     Aug. 5, 2021

Related U.S. Application Data

(60) Provisional application No. 62/663,713, filed on Apr. 27, 2018.

(51) Int. Cl.
A01H 1/08    (2006.01)
A01H 6/46    (2018.01)
A01H 1/04    (2006.01)

(52) U.S. Cl.
CPC .................. *A01H 1/08* (2013.01); *A01H 1/04* (2013.01)

(58) Field of Classification Search
None
See application file for complete search history.

(56) References Cited

U.S. PATENT DOCUMENTS 8,312,672 B2    11/2012    Deppermann et al.
2007/0117096 A1    5/2007    Ekstrom

FOREIGN PATENT DOCUMENTS

| WO | 2017011737 A1 | | 1/2017 |
|---|---|---|---|
| WO | WO 2017/011737 | * | 1/2017 |
| WO | 2017087682 A1 | | 5/2017 |
| WO | 2018052919 A1 | | 3/2018 |
| WO | WO 2018/052919 A1 | * | 3/2018 |

OTHER PUBLICATIONS

Chaikam et al., 2015, Analysis of effectiveness of R1 nj anthocyanin marker for in vivo haploid identification in maize and molecular markers for predicting the inhibition of R1 nj expression, Theor. Appl. Genet. 128: 159-171.*
Martins, et al., "Endosperm genotyping as a strategy to differentiate the allele source in maize heterozygous progeny," Pesq. agropec. bras., Brasilia, v.44, n.10, p. 1291-1296, out. 2009.
Conner, et al., "Haploid embryo production in rice and maize induced by PsASGR-BBML transgenes," Plant Reprod. Mar. 2017;30(1):41-52.
International Search Report and Written Opinion for International Application No. PCT/US2019/029204 dated Sep. 17, 2019.
Sleper et al. "Recombination and genetic variance among maize doubled haploids induced from F1 and F2 plants," Theoretical and Applied Genetics, Sep. 8, 2016 (Sep. 8, 2016), vol. 129, pp. 2429-2436.

* cited by examiner

*Primary Examiner* — Bratislav Stankovic
(74) *Attorney, Agent, or Firm* — Dentons US LLP; Amanda Carmany-Rampey

(57) ABSTRACT

The invention provides novel methods to genotype haploid embryos using molecular assays. For example, quantitative methods for genotyping are provided. The methods provided also include providing a plurality of haploid kernels, determining the genotype of the haploid embryo of said kernels by distinguishing its genotype from the endosperm genotype, selecting a kernel having a desired genotype and producing doubled haploid plant from the selected kernel.

19 Claims, 10 Drawing Sheets
Specification includes a Sequence Listing.

FIG. 5

Sample A
22T: 11C
{
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
}

In sample A, the ratio of T:C is 22:11. This corresponds to a 2:1 ratio for the two alleles and therefore the genotype of the haploid embryo is concluded to be "T."

The genotype of the corresponding haploid is "T"

Sample B
32C: 1T
{
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGTCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
...GCGCGGTATGTCTCTTGGCCTCTCAGTTTTTATCTGGT...
}

In sample B, the ratio of C:T is 32C:1T. Because the great majority of the reads are "C," the genotype of the embryo is C and the one read with "T" is likely due to contamination or sequencing error.

The genotype of the corresponding haploid is "C"

The region containing the middle SNP (T/G) that is polymorphic between the two chromosomes in the origin is not present in the HI.

FIG. 8

Genotype of origin parents and HI line

Origin parent 1:    ... GCGCGGTATGTCTCTTGGTTCTCTCTCCAGTTTTTATCTGGT ...
Origin parent 2:    ... GCGCGGTATGTCTCTTGGCCTCTCTCCAGTTTTTATCTGGT ...
HI parent 1 :       ... GCGCGGTGTGTCTCTTGGCCTCTCTCCAGTTTTTATCTGGT ...
HI parent 2 :       ... GCGCGGTGTGTCTCTTGGTCTCTCTCCAGTTTTTATCTGGT ...

The presence of a "G" in the HI lines instead of the "A" at a position near the "C/T" SNP marker of interest creates 4 microhaplotype alleles that can all be distinguished Sample A                                                                  Sample B Sequencing reads:                                                         Sequencing reads:

... GCGCGGTATGTCTCTTGGTTCTCTCTCCAGTTTTTATCTGGT                        ... GCGCGGTATGTCTCTTGGTTCTCTCTCCAGTTTTTATCTGGT
... GCGCGGTATGTCTCTTGGTTCTCTCTCCAGTTTTTATCTGGT                        ... GCGCGGTATGTCTCTTGGTTCTCTCTCCAGTTTTTATCTGGT
... GCGCGGTGTGTCTCTTGGTTCTCTCTCCAGTTTTTATCTGGT                        ... GCGCGGTGTGTCTCTTGGTTCTCTCTCCAGTTTTTATCTGGT
... GCGCGGTATGTCTCTTGGTTCTCTCTCCAGTTTTTATCTGGT                        ... GCGCGGTATGTCTCTTGGTTCTCTCTCCAGTTTTTATCTGGT
... GCGCGGTGTGTCTCTTGGCCTCTCTCCAGTTTTTATCTGGT                     ... GCGCGGTATGTCTCTTGGTTCTCTCTCCAGTTTTTATCTGGT
... GCGCGGTGTGTCTCTTGGCCTCTCTCCAGTTTTTATCTGGT                     ... GCGCGGTGTGTCTCTTGGTTCTCTCTCCAGTTTTTATCTGGT
... GCGCGGTGTGTCTCTTGGTCTCTCTCCAGTTTTTATCTGGT                         ... GCGCGGTGTGTCTCTTGGTCTCTCTCCAGTTTTTATCTGGT

In sample A, the ratio of T:C at the SNP of interest is 1:1 with few reads being detected, however, the only origin parent microhaplotype allele that is detected is "A, T" so the SNP in the haploid embryo at the position of interest can be determined to be "T" even though enough reads were not present to detect the expected 2:1 allele ratio.

In sample B, the only nucleotide detected at the SNP of interest is "T". In this case, the presence of the extra SNP nearby would not be required to make the call. However, with few reads, the direct observation of the origin parent specific microhaplotype allele increases confidence in the call.

The genotype of the                                                       The genotype of the
corresponding haploid is "T"                                              corresponding haploid is "T"

SEQUENCE LISTING

```
<160> NUMBER OF SEQ ID NOS: 4

<210> SEQ ID NO 1
<211> LENGTH: 39
<212> TYPE: DNA
<213> ORGANISM: Zea mays

<400> SEQUENCE: 1
gcgcggtatg tctcttggtt ctctcagttt ttatctggt                          39

<210> SEQ ID NO 2
<211> LENGTH: 39
<212> TYPE: DNA
<213> ORGANISM: Zea mays
```

```
<400> SEQUENCE: 2
gcgcggtatg tctcttggct ctctcagttt ttatctggt                          39

<210> SEQ ID NO 3
<211> LENGTH: 39
<212> TYPE: DNA
<213> ORGANISM: Zea mays

<400> SEQUENCE: 3
gcgcggtgtg tctcttggct ctctcagttt ttatctggt                          39

<210> SEQ ID NO 4
<211> LENGTH: 39
<212> TYPE: DNA
<213> ORGANISM: Zea mays

<400> SEQUENCE: 4
gcgcggtgtg tctcttggtt ctctcagttt ttatctggt                          39
```

METHODS FOR GENOTYPING HAPLOID EMBRYOS

CROSS-REFERENCE TO RELATED APPLICATIONS

This application is a 371 National Stage application of International Application No. PCT/US2019/029204, filed Apr. 25, 2019, which claims the benefit of U.S. Provisional Application No. 62/663,713, filed Apr. 27, 2018, each of which is hereby incorporated by reference in its entirety.

INCORPORATION OF SEQUENCE LISTING

The sequence listing that is contained in the file named "MONS433WO_ST25.txt", which is 1 KB (measured in MS-Windows) and created on Apr. 25, 2019, is filed herewith by electronic submission and incorporated herein by reference.

FIELD OF THE INVENTION

The present invention relates to the field of plant breeding and molecular biology. More specifically, the invention provides methods for genotyping haploid embryos and producing doubled haploid plants of a desired genotype.

BACKGROUND OF THE INVENTION

The use of doubled haploids (DH) in a plant breeding program allows new inbred populations to be created from desired parents in very few generations. In corn, haploids are created by crossing with a haploid inducer (HI). The majority of the progeny kernels are those that comprise diploid embryos, but a portion of kernels with haploid embryos are produced. Haploid seedlings are treated with chemicals to double the chromosome number, grown, and self-pollinated to produce diploid kernels. The diploid kernels represent a new line derived by the DH process. Although methods to distinguish and sort the haploid and diploid kernels have been developed, the production of doubled haploid plants remains a laborious and expensive process. Furthermore, not all of the haploid kernels will have a desirable genotype.

SUMMARY OF THE INVENTION

In one aspect, the present invention provides a method of obtaining a doubled haploid plant with a selected genotype comprising the steps of: a) providing a plurality of haploid kernels; b) determining the genotype of the haploid embryo of said kernels, wherein said determining comprises distinguishing the genotype of the haploid embryo from the endosperm genotype of the kernel comprising the haploid embryo; c) selecting a kernel having a desired genotype; and d) producing a doubled haploid plant from the selected kernel. In some embodiments, the determining the genotype comprises quantifying the alleles present in the endosperm of a given haploid kernel at a marker locus to determine the allele ratio present in said endosperm. In other embodiments, one or both the maternal and paternal parents of said haploid kernels are $F_1$ hybrids. In some embodiments, the quantifying the alleles present in the endosperm of a given haploid kernel at a marker locus comprises determining the alleles present at a higher ratio at said marker locus. In further embodiments, the determining the genotype comprises quantifying the alleles present at two or more marker loci. In even further embodiments, the quantifying comprises determining the alleles present at a higher ratio at said marker loci.

In some aspects, the methods disclosed herein further comprise inferring one or more alleles present at one or more markers associated with the genotypes of the haploid embryo and/or endosperm.

In another aspect, the present invention provides a method of obtaining a doubled haploid plant with a selected genotype comprising the steps of: a) providing a plurality of haploid kernels; b) determining the genotype of the haploid embryo of said kernels, wherein said determining comprises distinguishing the genotype of the haploid embryo from the endosperm genotype of the kernel comprising the haploid embryo; c) selecting a kernel having a desired genotype; and d) producing a doubled haploid plant from the selected kernel; wherein said determining comprises detecting in the endosperm the presence or absence of an allele in the haploid kernel. In some embodiments, the allele's DNA sequence is present in haploid kernels' origin parent and absent from the haploid inducer parent of the haploid kernels. In a further embodiment, wherein said allele sequence is polymorphic in the origin parent. In another embodiment, said determining comprises detecting in the endosperm the presence of said at least one allele sequence, wherein the allele sequence is a multiallelic polymorphism. In some embodiments, the multiallelic polymorphism is selected from the group consisting of single nucleotide polymorphisms (SNPs), insertions or deletions in DNA sequences (InDels), and simple sequence repeats of DNA sequence (SSRs). In further embodiments, the multiallelic polymorphism comprises a microhaplotype.

In another aspect, the present invention provides a method of obtaining a doubled haploid plant with a selected genotype comprising the steps of: a) providing a plurality of haploid kernels; b) determining the genotype of the haploid embryo of said kernels, wherein said determining comprises distinguishing the genotype of the haploid embryo from the endosperm genotype of the kernel comprising the haploid embryo; c) selecting a kernel having a desired genotype; and d) producing a doubled haploid plant from the selected kernel; wherein said determining comprises detecting in said endosperm at least one haplotype present in the haploid kernels.

In yet another aspect, the present invention provides a method of obtaining a doubled haploid plant with a selected genotype comprising the steps of: a) providing a plurality of haploid kernels; b) determining the genotype of the haploid embryo of said kernels, wherein said determining comprises distinguishing the genotype of the haploid embryo from the endosperm genotype of the kernel comprising the haploid embryo; c) selecting a kernel having a desired genotype; and d) producing a doubled haploid plant from the selected kernel; wherein said determining comprises identifying the nucleotide sequence present in said endosperm. In some embodiments, said identifying comprises an allele quantification assay. In further embodiments, the allele quantification assay is quantitative polymerase chain reaction (PCR). In another embodiment, the method further comprises comparing said nucleotide sequence to the genomic sequence present in either or both the parents of the haploid kernels.

In some aspects, the methods disclosed herein comprise providing a plurality of haploid kernels wherein said plurality of haploid kernels comprises at least 50, at least 250, at least 500, or at least 1000 haploid kernels.

BRIEF DESCRIPTION OF THE DRAWINGS

FIG. 2A shows the typical process to form a female gamete in maize. A diploid cell (2n) undergoes meiosis resulting in a 1n cell (1). That cell then divides further to form the megagametophyte (2) that contains several cells including the egg cell (EC) and the central cell (CC). In the CC, two nuclei are present so the CC has two sets of chromosomes whereas the other cells, including the EC, have a single set of chromosomes. Two sperm cells are present in each pollen grain (3). One sperm will join with the EC and another sperm will join with the CC. Because two nuclei are already present in the CC, the addition of the sperm nucleus results in a combined nucleus with three copies of each chromosome, indicated as "3n" (4). The CC divides to form the endosperm which has a 2:1 maternal to paternal ratio of chromosomes, whereas the embryo has a 1:1 maternal to paternal ratio. FIG. 2B shows the process to form a haploid kernel. In a haploid kernel, the endosperm forms with the typical 2:1 maternal to paternal ratio. In haploid kernels produced using stock 6 derivative haploid inducers (1), only the maternal chromosomes are present in the embryo. Using ig1 based haploid inducers (2), kernels are recovered that have endosperm with the typical 2:1 maternal to paternal ratio but only have the paternal chromosomes in the embryo. In the ig1 haploid kernels, the cytoplasm (mitochondria and plastids) is from the mother.

FIG. 3: Shows Endpoint TaqMan scatterplots for assays performed on a population of individuals for various cases to determine genotypes for haploid embryos in haploid induction crosses. In all illustrated cases, the TaqMan assays are designed to detect one allele in FAM (a1) and the other allele in VIC (a2). The position on the scatterplot for each assayed individual corresponds to the intensity for each color (FAM and VIC). Case #1 illustrates when both the origin parent and the haploid inducer are homozygous for the same allele of a given marker, signals from all endosperms tested will form a single cluster. Either all will be a1 (top) or all will be a2 (bottom). Case #2 shows situations where either the origin parent or the haploid inducer, but not both, are heterozygous for the two alleles of a given marker. In this case, signals from the population of endosperms that are tested will form two clusters. The genotype of the haploid embryo may be determined by identifying which cluster the data point from that individual is part of. Case #3 shows when both the origin parent and the haploid inducer are heterozygous for a given marker, the signals from endosperms of a segregating population of haploid kernels from those parents will form four clusters. The genotype of the haploid embryo may be determined by identifying which cluster the data point from that individual is part of.

FIG. 5: Shows an illustration of allele quantification using amplicon sequencing. A genomic sequence containing a SNP marker with two potential alleles, "T" (SEQ ID NO:1) and "C" (SEQ ID NO:2) is amplified from DNA extracted from the endosperm of two haploid kernels. Amplified DNA fragments are sequenced and the SNP allele assessed for each sequencing read. In Sample A, 22 sequencing reads contain the "T" allele and 11 sequencing reads contain the "C" allele. The "T" and "C" alleles are present in ~2:1 ratio, indicating that the "T" allele was contributed from the mother. Because the embryo and the endosperm both contain the same alleles contributed from the origin, the haploid embryo also has the "T" allele. In Sample B, 32 reads have the "C" allele and one read has the "T" allele. Because almost all reads have the "C" allele, the endosperm and therefore the haploid embryo have the "C" allele. The "T" read may result from sequencing error or from small amounts of DNA contamination introduced while harvesting tissue and extracting DNA from the endosperm or from other processes.

FIG. 8: Shows an illustration of microhaplotype detection to determine the embryo genotype. In this example, there are 4 microhaplotypes with a different nucleotide at each of two positions, "A" at the first position and "T" at the second (SEQ ID NO:1); "A" at the first position and "C" at the second (SEQ ID NO:2); "G" at the first position and "C" at the second (SEQ ID NO:3); or "G" at the first position and "T" at the second (SEQ ID NO:4).

DETAILED DESCRIPTION

Doubled haploid (DH) plants provide an invaluable tool to plant breeders, particularly for generating inbred lines. A great deal of time is spared as homozygous lines are essentially instantly generated, negating the need for multigenerational conventional inbreeding. In particular, because DH plants are entirely homozygous, they are very amenable to quantitative genetics studies. For breeders, DH populations have been particularly useful in QTL mapping, cytoplasmic conversions, and trait introgression. Moreover, there is value in testing and evaluating homozygous lines for plant breeding programs. All the genetic variance is among progeny in a breeding cross, which improves selection gain.

However, the DH production process is inefficient and can be quite labor-intensive. While double haploid plants can occur spontaneously in nature, this is extremely rare. Most research and breeding applications rely on artificial methods of DH production. The initial step involves the haploidization of the plant which results in the production of a population comprising haploid seed. Non-homozygous lines are crossed with an inducer parent, resulting in the production of both diploid and haploid kernels. Kernels that have a haploid embryo, but normal triploid endosperm, advance to the second stage. After selecting haploid kernels from the population, the selected kernels undergo chromosome doubling to produce doubled haploid kernels. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid testcross production.

Figure 1:
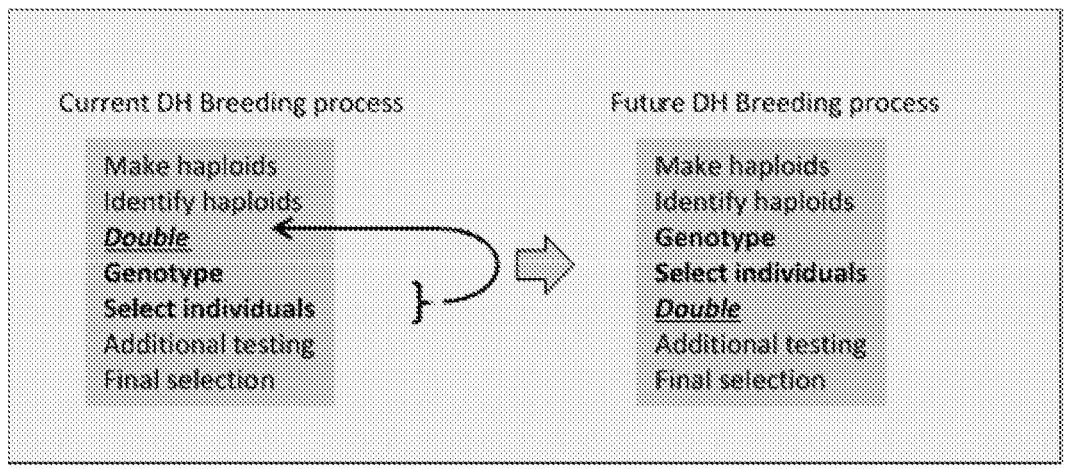
FIG. 1: Shows a schematic of the steps in the doubled haploid (DH) workflow and how the workflow changes when genotyping is performed prior to doubling.

Processes for producing DH seed generally suffer from low efficiency even though methods have been developed in an attempt to increase DH production frequency, including treatment with colchicine. Outstanding issues include reduced gamete viability resulting in diminished self-pollination for DH plant generation and inadequate DH seed yield for breeding applications. Furthermore, while advances have been made in the ability to obtain larger quantities haploid kernels, the doubling process remains slow and relatively expensive. The methods of the present invention represent a significant advance by allowing for selection at the haploid kernel stage, enabling the selection and regeneration of only the desired haploid kernels to advance to the doubling step, without the need to discard large numbers of regenerated plants of undesired genotypes (FIG. 1).

The present invention represents a significant advance in that it provides methods for determining the genotypes of the genetic markers of a haploid embryo without analyzing embryonic tissue, permitting the efficient production of double haploid (DH) plants having a desired, pre-determined genotype. The invention therefore significantly improves the efficiency of a DH breeding program through selection of desired genotypes at the haploid kernel stage, eliminating the need for costly production and testing of large numbers of DH plants of unknown genotype. By eliminating the need to regenerate substantial numbers of DH plants that would be discarded due to having of undesirable genotypes, resources can be more efficiently directed toward development of plants with desirable genotypes. This allows a reduction in the field and laboratory resources needed to identify and produce plants with desirable phenotypes and increases the capacity to evaluate much larger numbers of plants of a desired genotype for a given resource investment.

Figure 2:
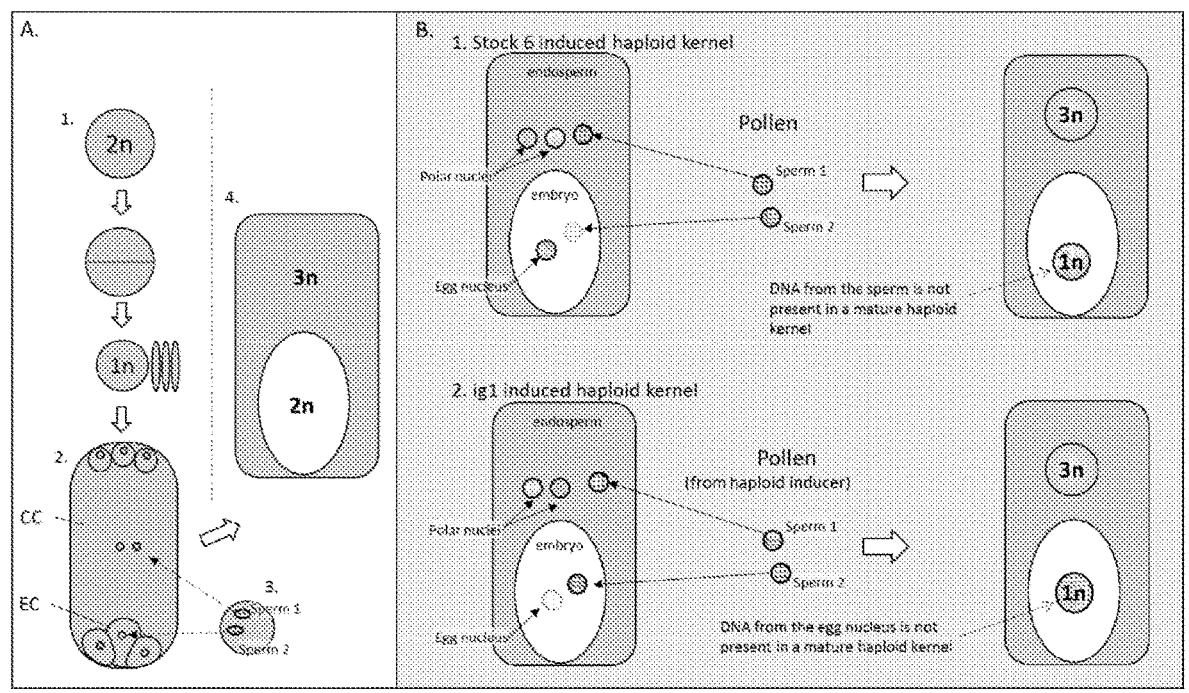
FIGS. 2A and 2B: Shows a diagram of normal (diploid) and haploid kernels and the chromosome ratios present in each.

In most plant genotyping methods, the tissue that is used to determine the genotype contains the same genetic material as the rest of the plant (with the exception of seed kernels). In the female reproductive structure, the megaspore divides several times to create the ovule. Because all the ovule's nuclei are derived from the megaspore, they are genetically identical. One of the cells, called the central cell, contains two identical nuclei. After fertilization, this cell will become the endosperm and the egg cell will become the embryo. In diploid kernels, the central cell and the egg cell each contain the same genetic material; thus, the genotype of the diploid embryo can be directly determined using tissue from the endosperm (FIG. 2A). However, determining the genotype of the embryo of a haploid kernel by assessing the endosperm requires additional steps beyond those that are adequate for a diploid kernel or plant tissue. In both haploid and diploid kernels, the endosperm tissue is triploid, with two chromosome sets derived from the female gamete and one chromosome set derived from the male gamete. The diploid embryo contains one chromosome set derived from the female gamete and one chromosome set derived from the male gamete; however, the haploid embryo contains only chromosomes from the non-haploid inducer gamete, which is typically the maternal gamete (FIG. 2B). In the endosperm, the two chromosome sets that originate from the female parent are identical to the chromosome set in the haploid embryo. Thus, genotyping markers of the haploid embryo is equivalent to identifying the female alleles of the markers in the endosperm of the same haploid kernel. The female alleles of markers in the endosperm can be determined by scoring the triple allele genotype of the endosperm (FF/M, where F and M are alleles of a marker, and/denote two separate chromosomes originating from female and male parent) or by exploiting the 2:1 female to male allele ratio of the endosperm. If the genotype of the endosperm is determined (e.g., AA/T, where A and T are alleles), then the allele that the haploid embryo has is A, and the allele the endosperm gets from the male parent is T. The methods provided herein enable one of skill in the art to reliably determine the genotype of a haploid embryo using endosperm tissue obtained from the kernels comprising the haploid embryo. Furthermore, the methods can also determine the allele that the endosperm gets from its male parent.

In specific embodiments, the methods provided by the invention include use of high throughput, non-destructive seed sampling to obtain endosperm tissue for genotyping. This sampling approach permits the rapid identification of seed comprising preferred or selected genotypes such that only preferred or targeted seed need be selected and advanced, saving resources on greenhouse and/or field plots. Apparatus and methods for the high throughput, non-destructive sampling of seeds have been described. For example, U.S. Patent Application Publication 20060048247; U.S. Patent Application Publication 20060048248; U.S. Patent Application Publication 20060042527; U.S. Patent Application Publication 20060046244; U.S. Patent Application Publication 20060046264; U.S. Provisional Application 62/523,072, and U.S. Patent Application Publication 20070204366, which are each incorporated herein by reference in their entirety, disclose apparatus and systems for the automated sampling of seeds as well as methods of sampling, testing and bulking seeds.

In some embodiments, the genotype associated with the maternal and paternal parents of the haploid kernel is determined. In corn, there are at least two haploid induction (HI) systems used commercially. The first is based on a haploid induction line that is used as the paternal parent. The induction lines of this system are derived from an original line called "stock 6." It has recently been shown that these lines contain a mutation in the phospholipase gene MTL1. Haploid kernels that result using these lines contain chromosomes from both the female plant (maternal parent) and the HI line (paternal parent) in the endosperm but only chromosomes from the female in the haploid kernel embryo. The second HI system is based on the haploid inducer as the maternal parent. Pollen from a line of interest is crossed onto a female HI line, which contains mutations to the Ig1 gene. A small percentage of the kernels that result will have haploid embryos with most of the haploid embryos containing chromosomes only from the male parent (a few of the kernels have haploid embryos containing only chromosomes from the mother). One of skill in the art would be able to utilize the methods provided herein to genotype haploid kernels produced from either HI system.

In one aspect of the invention, genotyping of a haploid embryo comprises assaying for one more genetic marker(s). "Marker," "genetic marker," "molecular marker," "marker nucleic acid," and "marker locus" refer to a nucleotide sequence or encoded product thereof (e.g., a protein) that is polymorphic at a genomic position between two chromosomes that an individual has and/or across different individuals. A marker can be derived from genomic nucleotide sequence or from expressed nucleotide sequences (e.g., from a spliced RNA, a cDNA, etc.), or from an encoded polypeptide, and can be represented by one or more particular variant sequences. A "marker probe" is a nucleic acid sequence or molecule that can be used to identify the presence of a marker allele, e.g., a nucleic acid probe that is complementary to a marker locus sequence. Alternatively, in some aspects, a marker probe refers to a probe of any type that can detect the presence of a particular allele at a marker locus. A "marker locus" can be used to track the segregation of a linked locus, e.g., a linked locus that encodes or contributes to expression of a phenotypic trait. For example, a marker locus can be used to monitor segregation of alleles at a locus, such as a quantitative trait locus (QTL), that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of single nucleotide polymorphisms (SNPs), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), or detection of amplified fragment length polymorphisms (AFLPs). Well established methods are also known for the detection of expressed sequence tags (ESTs) and SSR markers derived from EST sequences and randomly amplified polymorphic DNA (RAPD).

Genetic markers are distinguishable from each other (as well as from the plurality of alleles of any particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In general, most molecular markers rely on one or more properties of nucleic acids to determine their genotypes. Herein, nucleic acid analysis methods include, but are not limited to, PCR-based detection methods, microarray methods, mass spectrometry-based methods and/or nucleic acid sequencing methods. In some aspects, methods of the invention utilize nucleic acid amplification methods to detect/genotype a marker locus or loci. Such methods specifically increase the concentration of polynucleotides that span the polymorphic site, or include that site and sequences located either distal or proximal to it. Such amplified molecules can be readily detected by gel electrophoresis, fluorescence detection methods, or other means. "Amplifying," in the context of nucleic acid amplification, is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. In some embodiments, an amplification-based marker technology is used wherein a primer or amplification primer pair is admixed with genomic nucleic acid isolated from the first haploid kernel, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. An "amplicon" is an amplified nucleic acid, e.g., a nucleic acid that is produced by amplifying a template nucleic acid by any available amplification method (e.g., PCR, LCR, transcription, or the like). Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

Amplification is not always a requirement for marker genotyping (e.g. Southern blotting and RFLP detection may also be used). Separate detection probes can also be omitted in amplification/detection methods, e.g., by performing a real-time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. The genomic nucleic acid samples used include but are not limited to genomic nucleic acids isolated directly from a plant or seed, cloned genomic nucleic acids, or amplified genomic nucleic acids. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

Microarrays can also be used for polymorphism detection, wherein oligonucleotide probe sets are assembled in an overlapping fashion to represent a single sequence such that a difference in the target sequence at one point would result in partial probe hybridization. On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Detection of target sequences by microarray-based methods is known in the art.

Other methods for detecting polymorphisms, such as SNPs and insertions or deletions in DNA sequence (InDels), include single base extension (SBE) methods. Examples of SBE methods are known in the art. SBE methods are based on extension of a nucleotide primer that is adjacent to a polymorphism to incorporate a detectable nucleotide residue upon extension of the primer. In certain aspects, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In some embodiments, allele quantification can be performed by methods in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle, DNA polymerase with 5'→3' exonuclease activity cleaves the probe and separates the reporter dye from the quencher dye resulting in increased fluorescence of the reporter. A variety of reagents suitable for performing the methods described herein are commercially available, e.g., TaqMan™ from Applied Biosystems (Foster City, Calif.) as well as from a variety of specialty vendors such as Biosearch Technologies (Novato, Calif.).

In some embodiments, the marker locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

In alternative embodiments, in silico methods can be used to detect the marker locus or loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST™, or even simple word processors.

Any of the aforementioned marker types can be employed in the context of the disclosure to determine the genotype of the haploid embryo.

The 2:1 female to male allele ratio of an endosperm can be exploited quantitatively to determine the female and/or male allele of the endosperm, and various statistical and data mining methods including, but not limited to, likelihood based, Bayesian, machine learning, and artificial neuron network based methods can be used for this purpose. One specific method is to estimate the probabilities of all possible phased endosperm genotypes (e.g., AA/A, AA/T, TT/A, and TT/T, where A and T denote two alleles of the marker) using all available data including, but not limited to, information of the marker under study, pedigree, and parental and ancestral genotypes. The female and/or male allele of an endosperm can be scored if the normalized likelihood of being a specific allele is above a pre-specified threshold. In practice, it is common to include some quality control measures and to model some error terms including, but not limited to, sequencing in the analysis. Common quality control measures including, but not limited to, verifying that the kernel is a haploid kernel and its listed parents are the correct parents of the haploid kernel.

Information of multiple associated, especially linked, markers can be jointly used to determine the female and/or male allele of an endosperm. The different types of markers that can used for this purpose are including but not limited to SNP and InDel markers. In some cases, multiple markers with insufficient data to call genotypes based on their own data can be jointly evaluated to determine their genotypes. Different data types at different markers for individuals (e.g., an individual has AA genotype at marker 1 and five sequence reads of G allele at marker 2) can be jointly evaluated to determine their genotypes. In many cases, the genotype of a marker can be imputed based genotypes of linked markers and/or genotypes of related individuals. Also, different statistical and data mining methods including, but not limited to, likelihood based, Bayesian, machine learning, and artificial neuron network based methods can be used to perform these joint analyses.

In one aspect of the invention, genotyping of a haploid embryo comprises determining the specific alleles present in the haploid embryo for markers that were not directly assessed with molecular methods. In this case, the alleles for a subset of desired markers are identified using the various methods provided herein, including methods where allele ratios are not used. The remaining desired markers are determined from the subset using one or more mathematical or logical approaches based on the principles of genetic linkage. Some of these approaches are known as imputation or inference.

In some embodiments, determining which of two possible homologous polymorphic genomic regions or haplotypes from the origin is present in the haploid is accomplished by identifying which allele is present in the haploid for one or more diagnostic markers in the said genomic region or haplotype. Once the specific region or haplotype in the haploid is determined, the allele present for other markers in that specific region or haplotype may be inferred.

Performing whole genome sequencing (WGS) from endosperm DNA for a haploid kernel may result in one or more sequences corresponding to several markers which are polymorphic between two possible homologous polymorphic genomic regions or haplotypes from the origin. In cases where WGS is done at low coverage, sequence coverage will be absent for many markers which are polymorphic between the genomic regions or haplotypes of interest. For markers with sequence coverage, the number or reads may be a few or only one and with low coverage, the likelihood of sequencing error is high. By comparing reads from a plurality of markers within the polymorphic genomic region or haplotype to the origin, it is possible to determine which specific polymorphic genomic region or haplotype from the origin is present in the endosperm. In making this determination, the presence of DNA from the HI should also be considered. For example, sequences that are unambiguously from the origin may be considered as stronger evidence than sequences which could be either from one region in the origin or from the homologous region in the HI.

One of skill in the art will understand that all or part of the genome of the haploid can be inferred or imputed using an adequate number of markers that are directly determined using methods provided herein and reference genomes. The degree of completeness and accuracy of the inferred or imputed genome of a haploid depends on both 1) the availability of adequate genome information for the origin, lines in the origin's pedigree or reference genomes and 2) the number, distribution and accuracy of determination for the markers used for inference or imputation.

Definitions

An "allele" refers to one or more alternative forms of a genetic sequence; the length of an allele can be as small as 1 nucleotide base. It can also refer to the absence of a sequence. For example, a first allele can occur on one chromosome, while a second allele occurs on the homologous position of a second chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome site or segment is a chromosome site or segment that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, embryos, seeds or plants) and includes crosses between plants (sexual) and self-fertilization (selfing).

"Genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome, or its entire genetic makeup. The terms "phenotype," or "phenotypic trait" or "trait" refers to one or more traits of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of the expression of several genes and their interaction with environments.

"Haploid Inducer (HI)" refers to a variety or individual that induces formation of haploid embryos when used in genetic crosses. "HI cross" refers to the act of combining gametes (i.e. sperm, the egg and central cell) from a HI to gametes of a non-HI line to produce kernels. In corn, HI lines are commonly derived from two sources, Stock 6 and ig1. In the case of Stock 6 derivatives, the HI is used as the male in HI crosses to produce kernels that have haploid embryos with genomes that comprise genetic material only from the egg and not from the sperm. In these haploid kernels, the endosperm genome comprises the typical combination of maternal and paternal chromosomes found in normal diploid kernels. This typical combination includes two sets of chromosomes from the mother (that are the same as those found in the egg) and a single set of chromosomes from a sperm. In the case of ig1 HIs, kernels may be recovered that contain embryos with chromosomes from a sperm but not from the egg. In these haploid kernels, the embryo contains the chloroplast and mitochondria from the mother and the chromosomes from the father. As with Stock 6 derivatives, the endosperm contains the typical combination of maternal and paternal chromosomes found in normal diploid kernels. Other HIs have been described or may be developed. Another HI line was reported where the haploid induction effect was accomplished by expressing a modified CenH3 gene. In other plants, HIs have been created by modifying other genes and these approaches may be applied to corn. Furthermore, haploid induction has been reported by applying oil to ears during crosses. In this case, the HI may be a standard corn line that without the oil application would otherwise not produce haploid kernels at a useful rate. When used in commercial applications, the HI is often a hybrid between two HI lines. A hybrid HI may be used in these cases because hybrids exhibit more agronomically valuable properties than inbreds including more vigorous growth and more abundant pollen production. "HI parent" may refer to an HI line that is used as a gamete source (typically pollen) to create a haploid kernel or one of two HI lines that are crossed to make a hybrid HI line.

A "locus" is a position on a genomic sequence that is usually found by a point of reference; e.g., a short DNA sequence that is a gene, or part of a gene or non-genic region. The loci of this invention comprise one or more polymorphisms in a population; i.e., alternative alleles present in some individuals.

A "haplotype" is defined by the combination of alleles of markers located in a chromosome interval that allow the interval to be distinguished from homologous intervals. The size of the chromosome interval defined for a haplotype is determined with reference to a given population and is intended to provide a practically useful way to catalog different homologous chromosome segments within the population. For example, if a large and genetically diverse population is considered, haplotypes may comprise a short genetic distance (a few centimorgans to less than a centimorgan) whereas in a smaller population, the genetic length of a haplotype may be longer resulting in a manageable number of different haplotype variants for a given chromosome segment. As used herein, "microhaplotype" refers to the combination of alleles of two or more markers that are close enough to each other that they can be detected using a single molecular assay such as sequencing a DNA molecule or conducting a TaqMan-like assay.

"Origin" refers to the origin plant that is used in a cross with the HI to produce haploid kernels. A haploid kernel will contain an embryo with a genome inherited from the origin line but not the HI genome. In some embodiments, two high performing lines are crossed to make a hybrid which is then crossed with a HI. In this embodiment, the said hybrid is the "origin" or "origin parent" in the HI cross. In HI crosses made with Stock 6 derivatives, the origin is the female plant. In HI crosses made with ig1 based inducers, the origin plant is used as the pollen source and crossed on to an ig1.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, "polymorphism" means the presence of one or more variations of a nucleic acid sequence at one or more loci in a population of one or more individuals. The variation may comprise but is not limited to one or more base changes, the insertion of one or more nucleotides, a repeat, or the deletion of one or more nucleotides. A polymorphic locus may be as small as one base pair. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms. A multiallelic polymorphism has two or more forms. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In addition, the presence, absence, or variation in copy number of the preceding may comprise polymorphisms. A polymorphic marker or site is the locus at which variation occurs. Multiallelic markers may include SNPs or Indels with three or more possible alleles.

As used herein, "quantifying alleles" refers to determining the ratio of two different alleles at a given locus in an individual. This may be done by performing TaqMan reactions and analyzing the scatterplots of data from a segregating population, amplicon sequencing and counting the number of reads for each allele, dPCR, qPCR, Invader, array binding intensity or other methods. For the purpose of identifying the allele for a given marker in the endosperm that is from the mother, an approximate 2:1 maternal to paternal ratio is expected for a given marker.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1: Development of Quantitative Assays for Haploid Embryo Genotyping

There is typically a 2:1 ratio of maternal DNA to paternal DNA in the endosperm of a haploid kernel. In most cases, the maternal parent is the non-haploid inducer (HI) plant and therefore contributes genetic material to the endosperm and to the haploid embryo. Accordingly, the paternal parent is typically the HI plant and contributes genetic material to the endosperm only. Genotyping methods that detect the ratios of alleles can be used to identify which parent contributed a given allele. As the HI line is the paternal contributor (in the case of "stock 6" derived HI lines), alleles present in the endosperm at the higher ratio are from the maternal genome and will be present in the embryo. In cases where the maternal line is homozygous for a given allele, that allele will be present in the haploid embryo.

Figure 3:
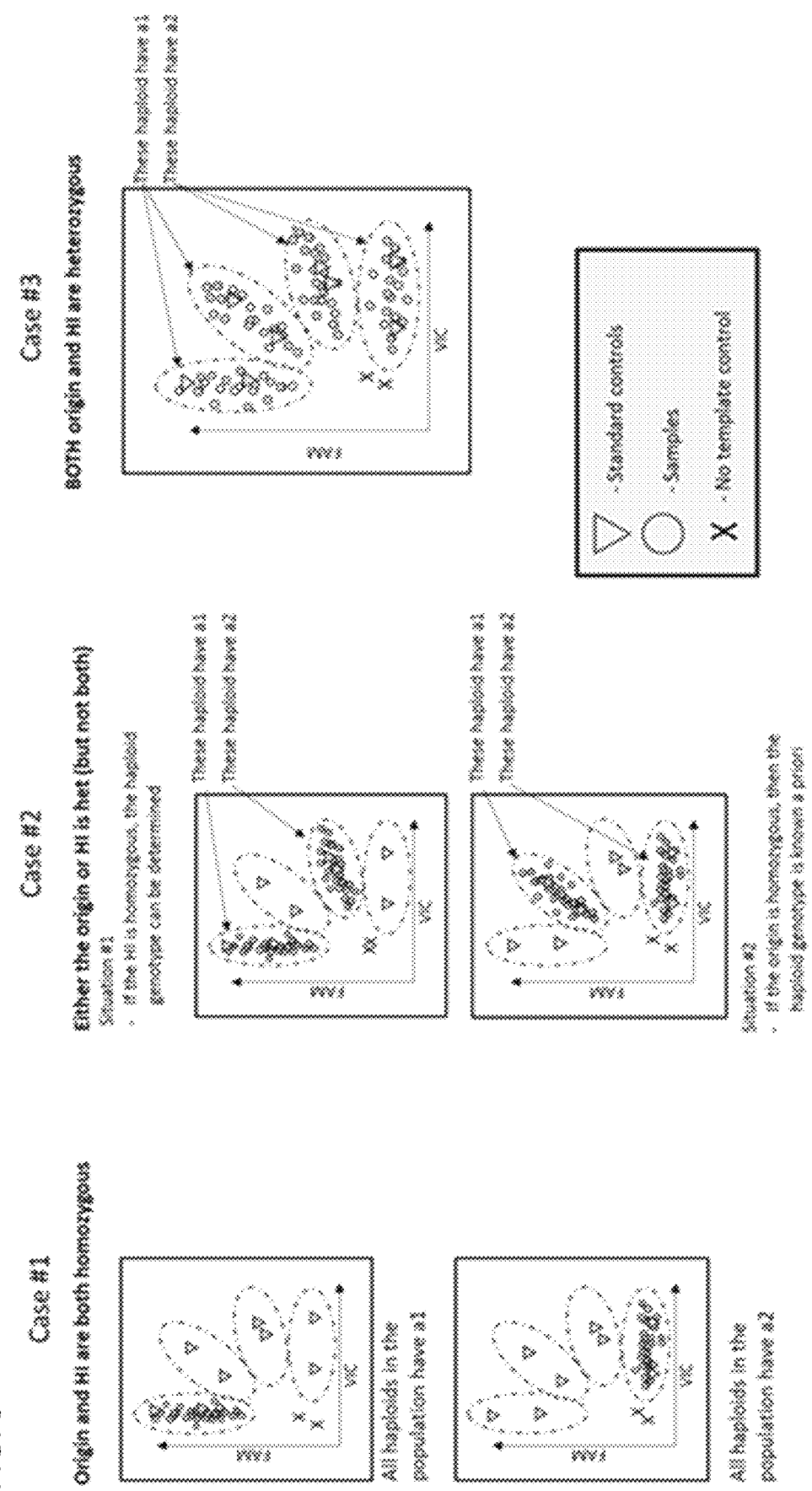
Figure 4:
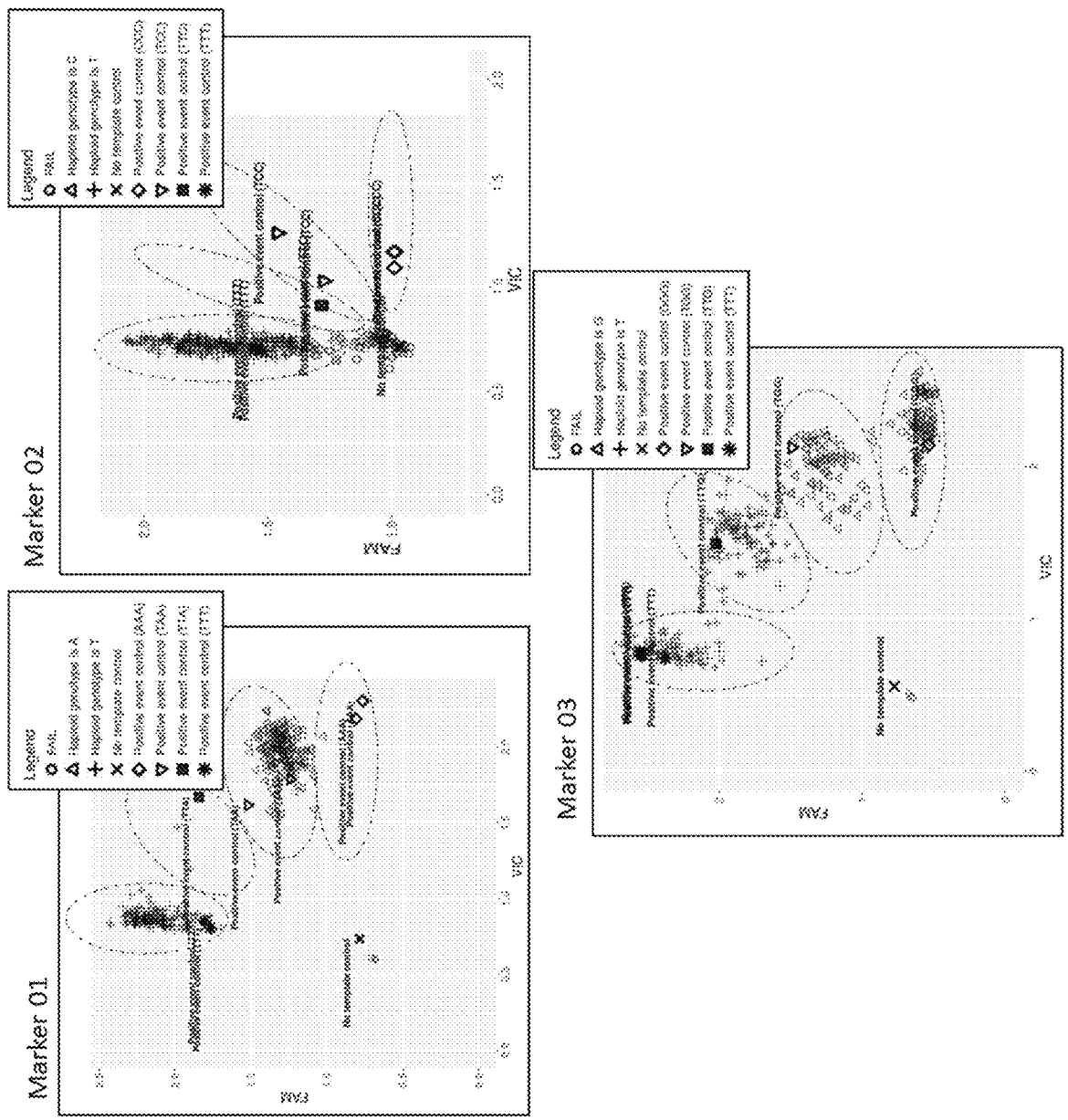
FIG. 4: Shows three scatterplots produced from TaqMan assays performed on DNA from endosperm tissue from a population of haploid kernels. In the first case, the SNP marker "Marker 01" is known to have alleles "A" and "T," for the origin and only the "A" allele in the HI. Based on the cluster that each individual is part of, the alleles in the endosperm may be quantified as either 3:0 ("AAA") or 2:1 ("TTA") and the genotype of the haploid embryo determined ("A" or "T"). In the second case, the SNP marker "Marker 02" is known to have two alleles, "C" and "T." When TaqMan assays were performed on DNA from the endosperm for a population of haploid kernels, the data points formed a single cluster. By including control samples with known allele ratios, it was possible to determine that all the individuals only had the "C" allele present in the endosperm and therefore the haploid embryo genotype for this marker is "C" in all cases where data was generated. In some samples, the assays produced a very low signal and was scored as "FAIL." In the third case, the SNP marker "Marker 03" is heterozygous for the "G" and "T" alleles in both the origin and HI. TaqMan data points for DNA from endosperm tissue of haploid kernels formed four clusters. Haploid kernels corresponding to data points in the top two clusters have the "T" allele in the haploid embryo and haploid kernels corresponding to the bottom two clusters have the "G" allele.

End-point TaqMan assays were designed to determine allele ratios at single markers in several individuals from a population using the rationale described above. For a given pair of alleles (a1 and a2) at a single marker, there are four possible ratios of a1:a2 in the endosperm: 3:0, 2:1, 1:2, and 0:3. Because the mother contributes two copies of an allele, the ratios of the maternal allele will be either 2:1 (if the mother and father contribute different alleles) or 3:0 (if the mother and father contribute the same allele). End-point TaqMan assays produce fluorescence in two colors and the intensity of the colors is proportional to the marker ratio in the sample tested. The assay is performed on a several individuals from a population and the fluorescence intensity corresponding to the two alleles is plotted—one allele's fluorescence intensity on the X-axis and the other on the Y-axis. The points corresponding to the different allele combinations form clusters that can be distinguished from each other. Based on the cluster that a given individual's assay is grouped with, the allele ratio (and thus, the genotype of the endosperm at the marker being assayed) can be determined (FIG. 3). The results for assays designed for markers Marker 01, Marker 02, and Marker 03 are shown in FIG. 4. Genotyping by detection of allele ratios for individual markers may be done using any quantitative method known to one of ordinary skill in the art, including but not limited to qPCR, Invader, digital PCR (dPCR), and nanopore detection.

Quantitative genotyping methods may be multiplexed to determine allele ratios for multiple markers. Multiplex amplicon sequencing was performed to demonstrate that amplicons can be quantified and compared to determine allele ratios. For amplicon sequencing, approximately 1300 amplicons were generated using the AmpliSeq multiplex amplicon sequencing method. A pool of 1300 PCR primers were designed to amplify SNPs. DNA from haploid kernels' endosperm was extracted and used in a PCR reaction with the SNP-specific primers. After processing the PCR products, which included removing primer dimers and adding sample barcodes, the amplicons were sequenced. The amplicons that corresponded to each sample were identified by the barcode sequence. To assist in analyzing the sequencing data, an algorithm was developed that used amplicon count ratios to determine the maternally contributed marker allele. The count of the two SNP variants was determined for each marker. If the ratio of the two SNP variants was approximately 2:1, it was concluded that the haploid embryo had the SNP variant that was more abundant (FIG. 5). The algorithm may be applied to amplicons produced using other methods known in the art, including but not limited to Roche HeatSeq (MIPs), Affymetrix's Eureka method, Illumina's TruSeq method, rhPCR from IDT, MegaPCR, and iGenomX's targeted library prep method.

Microarrays may also be used as a quantitative genotyping assay that is highly multiplexed. The Infinium array method collects fluorescence intensity for each marker in a set. For each marker, a different color is used to detect each allele and the fluorescence intensity that is detected is proportional to the number of copies of the respective allele. The relative fluorescence intensity measurements are used to determine if a marker is homozygous for one or the other allele, or heterozygous. The method was applied to haploid kernels by determining which allele was present at higher copy number in cases where both alleles are detected to be present. Haploid induction crosses were performed using two non-HI lines, where the parents are 43.5% identical by descent and 65.3% identical by descent. The HI line in both cases was INA116/INA124. Haploid kernels were identified by phenotypic screening. The kernels were then sampled and the genotype of the endosperm was determined for two kernels from each origin. The kernels were germinated and leaf tissue from the germinated haploid plant was obtained and genotyped so that the accuracy of methods to determine the genotype of the haploid from the endosperm could be assessed. Control samples were included from hybrid individuals where the DNA was taken from diploid leaf tissue. In the control samples, the allele frequency of polymorphic cases is 1:1. By comparing the relative fluorescence intensity of markers that are heterozygous in diploid tissue to the relative fluorescence intensity of the same markers run from haploid kernels, it could be determined which allele was present as two copies compared to one copy.

Example 2: Development of Marker Assays Based on Variations Observed in Progenitors to Determine Haploid Embryo Genotype Substantial variation is known to exist among corn lines—including the presence or absence of many sequences. Loci where variation is present between the two progenitors of origin as well as between the loci in the origin progenitors and the loci in the haploid inducer may be used as markers. In these cases, all the variants of a given locus can be differentiated using appropriate assays and the marker present in the haploid embryo can be determined by assaying the endosperm as described herein.

Figure 6:
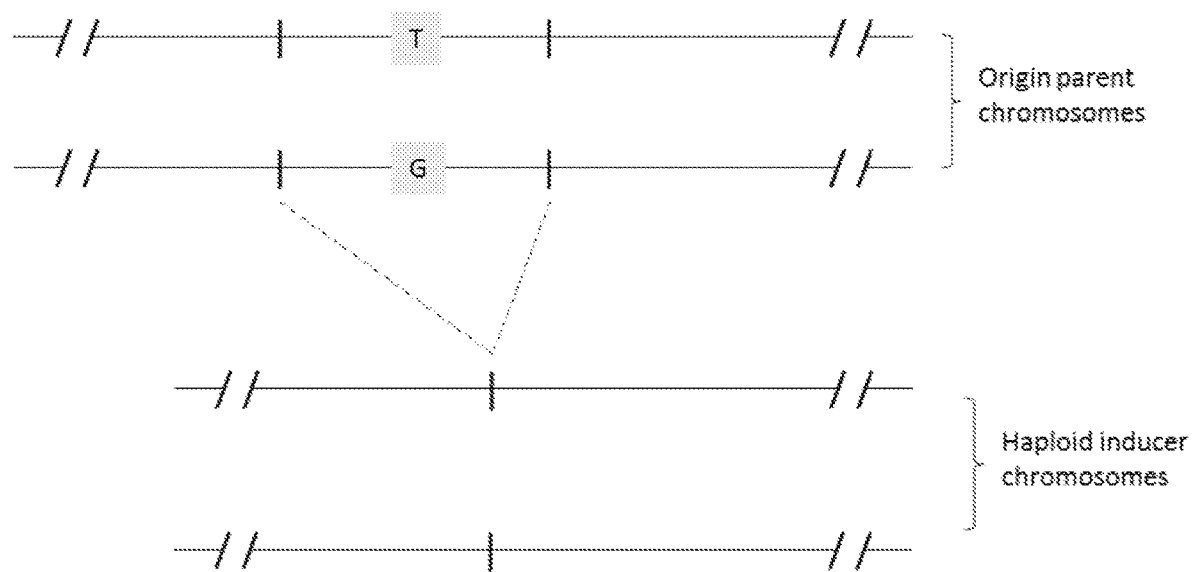
FIG. 6: Shows an illustration of how sequence variation and genome structural variation results in missing markers that can be exploited for genotyping haploid kernels.

One example is use of a locus comprising a polymorphic sequence that is present (namely having the insertion allele) in the origin and both variants are absent (namely having deletion homozygote) in the haploid inducer (FIG. 6) to determine the genotype of the haploid embryo (Table 1). In FIG. 6, a locus presented comprises a sequence where the middle SNP marker ("T"/"G") is polymorphic in the origin.

A HI comprising a variant of the locus that lacks the sequence may be identified and used to produce haploid kernels with the origin. The endosperm of a haploid kernel that is produced from that HI may be assessed for the marker and the allele detected in the endosperm will be in the haploid embryo. A TaqMan assay, for example, may be designed to detect the "T" or "G" alleles. Because the sequence is missing in the HI chromosomes but are present in the endosperm, the primers used in the TaqMan assay will only amplify the sequence from the origin. HI lines that lack specific markers of interest can be generated by finding lines that lack the marker sequence and performing backcrossing or other trait conversion crossing strategies to move the region lacking the marker into the HI background. Alternatively, gene editing or mutation methods may be applied to remove or alter the marker sequence present in a HI. A HI line may be generated that lacks a substantial number of genomic sequences corresponding to markers of interest. This line may be used to genotype haploid kernels without the need to quantify alleles.

TABLE 1

Genotyping of haploid embryo using endosperm and progenitor data[1,2,3]

| Origin | | Inducer | | Alleles | |
|---|---|---|---|---|---|
| Progenitor 1 | Progenitor 2 | Progenitor 1 | Progenitor 2 | detected in endosperm | Haploid embryo |
| T | G | D | D | T | T |
| T | G | D | D | G | G |
| T | G | T | T | T | unknown |
| T | G | T | T | T, G | G |
| T | G | T | T | G | G |
| T | G | T | T | unknown | unknown |

[1]T, G denote two alleles of the polymorphism in insertion allele
[2]D, deletion allele
[3]unknown, information missing Shown in Table 1 are examples of joint use of progenitor and endosperm data to determine the genotype of the haploid embryo. In this instance, the marker has three alleles: T, G, and D for deletion, which is a special case of multiallelic marker. Deletion can be both unobservable (e.g., the entire amplicon is within deletion segment) and observable (e.g., primers are designed to generate the amplicon that include substantially long sequence on both sides of the deletion).

Figure 7:
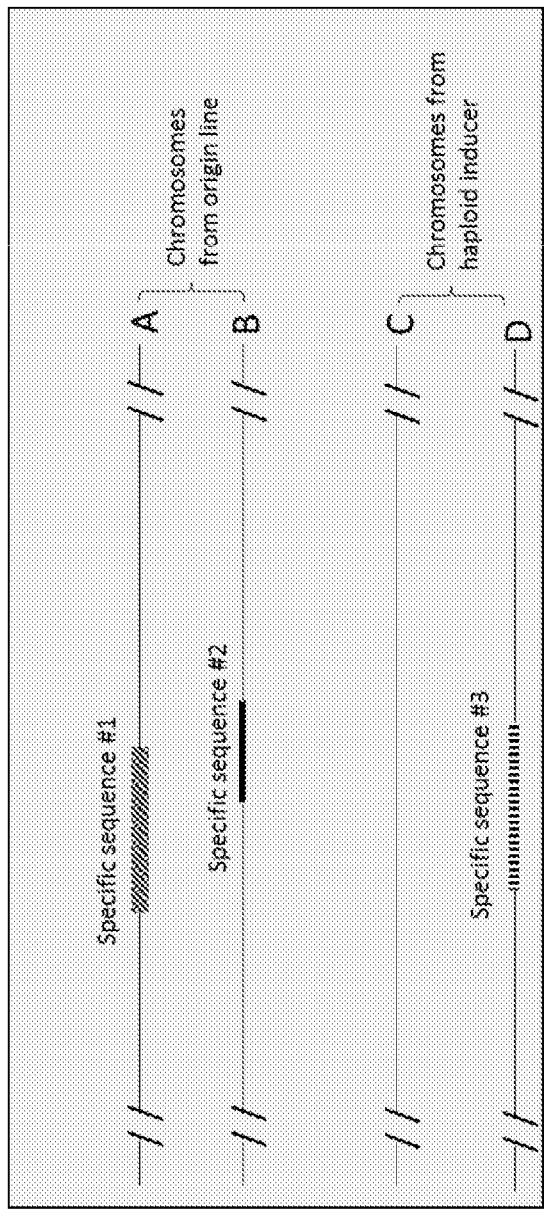
FIG. 7: Shows an illustration of how sequences present in one but not both of the origin's parents may be used as dominant markers for genotyping haploid kernels. In this illustration, two homologous chromosome segments in the origin contain different alleles. The alleles differ by the presence of a specific sequences found only in the "A" or "B" alleles respectively. In the HI, two additional alleles are present at the homologous chromosome segment—one of the alleles, "D" contains a specific sequence not present at the other alleles. The other allele in the HI lacks the various allele specific sequences present at the other three alleles.

Another example involves three specific sequences in a small genome segment (FIG. 7). In this instance, four progenitors of the origin and inducers contains four different microhaplotypes. This polymorphism can be viewed as different types of markers depending the assays used to detect these microhaplotypes. If three probes were designed to detect these three specific sequences, they become three dominant markers in vicinity. If the segment that contain all three specific sequences, it become one marker with a total of four alleles. Also, two to three SNP markers can be designed to distinguish these four microhaplotypes: allele combinations of these two or three markers would naturally form the microhaplotypes and be used to genotype endosperm and haploid embryo. In each case, joint use of progenitors and endosperm would achieve more efficient genotyping of haploid embryo.

Another example is use of sequences found only in one of the progenitors of the origin and absent in the progenitors of the haploid inducer as dominant markers. Detection of an origin progenitor-specific marker in the endosperm tissue indicates that a specific genomic region is present from the respective progenitor or that there is sample contamination. Optimally, dominant markers are selected so that pairs of marker, one from each origin progenitor, may be assayed for each genetic region of interest (FIG. 7). After generating and sorting haploid kernels by crossing the HI line onto a hybrid female made up of the two origin parents, kernels will be assayed for the presence of the two parent specific sequences. In Table 2 below, hypothetical results of assessing endosperm DNA of three samples for the presence or absence of the allele specific sequences are presented. In Sample 1, the first specific sequence is detected in the endosperm, indicating that both the endosperm and haploid embryo will have specific sequence 1 (SS1). In Sample 2, the second specific sequence is detected in the endosperm, indicating that both the endosperm and haploid embryo will have specific sequence 2 (SS2). The third specific sequence is also detected in the endosperm but because the chromosomes from the inducer will not be present in the haploid embryo, the haploid embryo will only have specific sequence 2 (SS2) present. In Sample 3, specific sequence 3 (SS3) is detected. Since specific sequence 3 (SS3) is from the HI, it will not be present in a haploid embryo. In this case, this data does not allow the genotype of the haploid embryo to be determined.

TABLE 2

Potential Outcomes and the Corresponding Interpretation of Results[1]

| | Origin | | Inducer | | | |
|---|---|---|---|---|---|---|
| Sample | Progenitor1 | Progenitor2 | Progenitor1 | Progenitor2 | SS detected in endosperm | Haploid embryo |
| 1 | SS1 | SS2 | None | SS3 | SS1 | SS1 |
| 2 | SS1 | SS2 | None | SS3 | SS2, SS3 | SS2 |
| 3 | SS1 | SS2 | None | SS3 | SS3 | unknown |

[1]SS denotes specific sequence

Tri-allelic and tetra-allelic SNPs (loci with three and four alleles known to be present at the variant nucleotide position) have been identified in corn lines and may also be used as markers. Sequence based method can directly measure the nucleotide at the multi-allelic SNP to determine genotypes of endosperm. With help of the genotype of the progenitors of the origin and/or the inducer, haploid embryo genotype can be efficiently determined.

Genotyping of the haploid embryo at such SNP loci may be accomplished using PCR-based assays, such as TaqMan, rhAmp-SNP, KASP, and molecular beacons. When designing such assays, probes for the two SNP alleles present in the progenitors of the origin are the only ones necessary to determine the genotype of the haploid embryo. However, a third (or fourth) probe may be included to detect the haploid inducer allele, if desired. Alternatively, targeted sequencing of the marker may be used to detect the SNP allele present in the endosperm tissue.

Microhaplotypes may also be used as markers. Such marker variants can be unambiguously identified as coming from one of the progenitors of the origin or the progenitors of the haploid inducer so long as the various combinations of marker variants are distinct among the potential progenitor lines. The genetic variation that comprises the individual variants of a microhaplotype may include SNPs, InDels, SSRs, or other genetic variation. Detection of the microhaplotype variants may be accomplished by sequencing methods known in the art or by methods described herein. In cases where a hybrid HI parent is used to produce haploid kernels, the microhaplotype alleles of the two progenitors of the HI parent may be either different or identical to each other but they must both be different from the two origin progenitors.

Amplicon sequencing was performed to demonstrate use of microhaplotype alleles as markers for haploid embryo genotyping. A pool of PCR primers was designed to detect genetic markers comprised mostly of SNPs and a few InDels. DNA was extracted from haploid kernels and used as a template in a multiplex PCR reaction. The resulting amplicons were sequenced and analyzed to determine the genotype of the endosperm using allele frequency ratios (described in Example 1). To demonstrate the potential of using microhaplotypes for discriminating alleles from the HI line from those from an origin parent, the sequence data was analyzed to identify cases where additional SNPs, InDels, or other variations were present in amplicons. The additional sequence variants present in the amplicons allowed further discrimination of SNP alleles that were identical between the HI line and an origin parent (FIG. 8).

Figure 9:
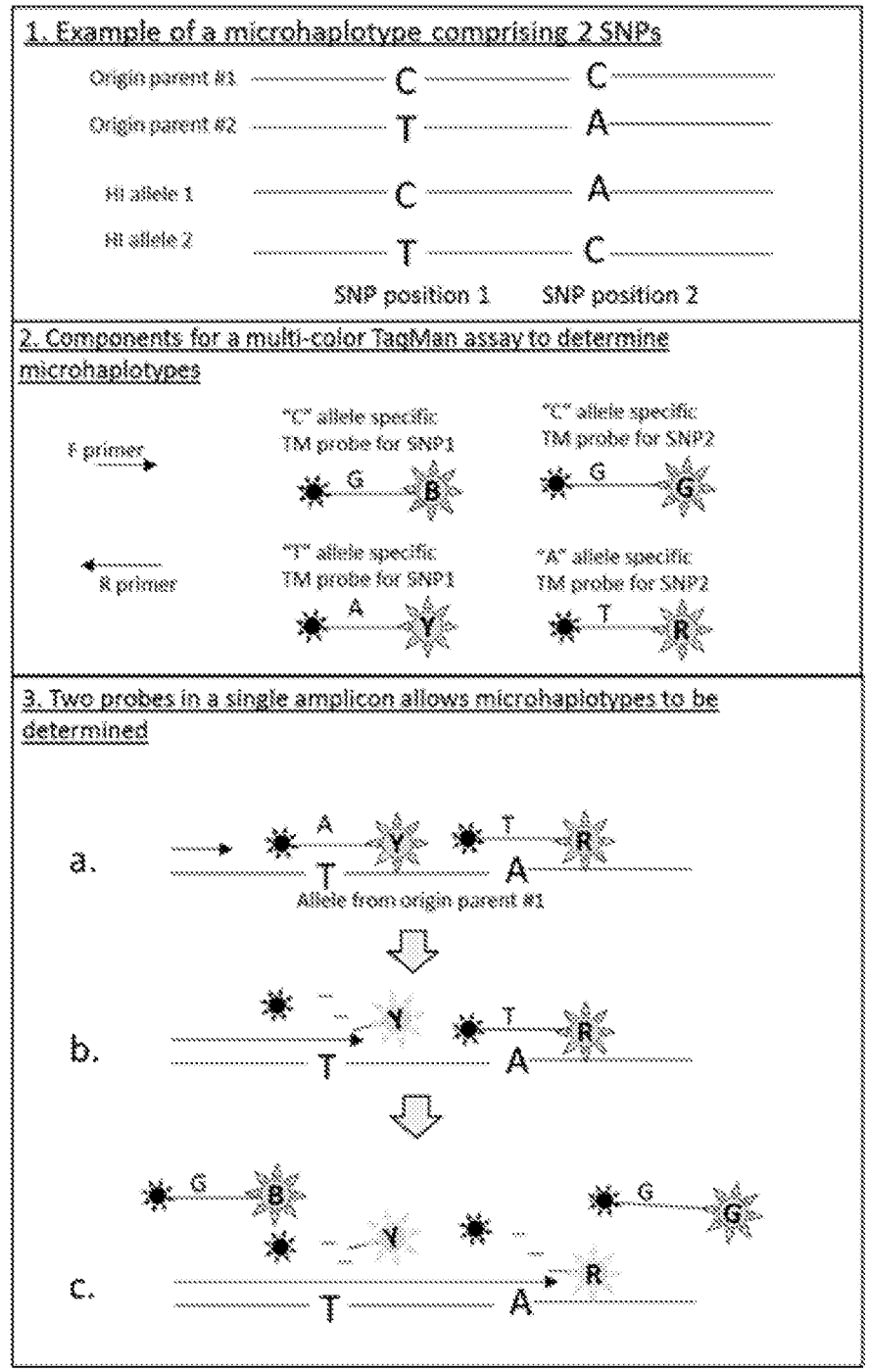
FIG. 9: Shows an illustration of using a multicolor TaqMan-like assay to differentiate between microhaplotypes. In this example, the origin contains two microhaplotypes or alleles at a given genomic location, one from each of its parents, where each microhaplotype has a different nucleotide at each of two positions. The HI has the other two SNP combinations for a total of four distinct microhaplotypes: (1) PCR primers (F primer and R primer) as well as two pairs of probes are used to perform a TaqMan assay. The two pairs of probes correspond to the two SNP positions and each probe is a distinct color; (2) A PCR reaction is performed with the probes present in the reaction; (3) During the PCR reaction, the probes hybridize to the complementary SNP (a) and are hydrolyzed during strand extension to activate fluorescence (b)-(c).

Detection of microhaplotypes may be accomplished using molecular assay other than sequencing. For example, if the SNPs that comprise the microhaplotype are close enough together, multicolor assays that differentiate the microhaplotypes may be designed and utilized using the methods described herein. In this case, a single primer pair may be utilized to amplify the allele of interest, as in a typical TaqMan reaction, but may also include two probe pairs in the reaction instead of a single probe pair as is typical of SNP TaqMan assays. Each of the four probes may be labeled with a different dye so that upon amplification, the presence of each SNP is detected by the respective fluorescent color. Two probe pairs and four colors are used that detect the SNPs that constitute the microhaplotype. FIG. 9 shows an example where the microhaplotype alleles of the two origins are "C, C" and "T, A" and the microhaplotype alleles present in the HI are "C, A" and "T, C." In the microhaplotype, the first SNP is C or T and is detected with blue (B) and yellow (Y), respectively, and the second SNP is C or A and is detected with green (G) and red (R), respectively. Table 3 below shows the 4 possible combinations (samples 1-4) of the two maternal and two paternal alleles present in the endosperm and the color combinations that result from detection with the four probes. All four allele combinations are detected with a unique color combination.

TABLE 3

Combinations of Contributed Alleles and Corresponding Color Combinations

| Sample # | Origin contribution to endosperm and embryo | HI contribution to endosperm | Colors detected by genotyping endosperm |
| --- | --- | --- | --- |
| 1 | C, C | C, A | B, G, R |
| 2 | C, C | T, C | B, Y, G |
| 3 | T, A | C, A | B, Y, R |
| 4 | T, A | T, C | Y, R, G |

Alternatively, a primer pair may be designed that discriminates against a SNP, InDel, or other variation that is present in only the HI parent to limit amplification to only the origin alleles of another nearby SNP. For example, a primer may be designed such that a mismatch would occur at or near the 3' end of the oligo at the, e.g., SNP that is present in the HI line but not in the origins. A primer pair may also be designed that that comprises an allele-specific primer for a first SNP and a probe for a second SNP, which will allow amplification and detection of a signal only if both the first and second SNP are the variants specified by the primer and probe. This will allow the SNP that is part of one of the two origin microhaplotypes to be detected without interference by the SNP from the HI line. Primer pairs may also be designed that comprise allele-specific primers and sequences for the detection of universal probes. Alternatively, universal probe sequences could be added to both the forward and reverse primers.

Example 3: Development of Comparative Assays for Determination of Haploid Embryo Genotype When an $F_1$ hybrid origin is used to create haploid kernels, each chromosome in the haploid has only gone through a single meiosis in a hybrid state. In each meiosis, only 0, 1 or a couple of crossovers per chromosome arm are expected so most allele variants are in blocks that match one of the parents. Thus, adjacent markers can provide additional information that allows ambiguous genotyping situations to be clarified. If several markers are considered for a given genetic or genomic region, it is possible to determine which parent of the $F_1$ hybrid contributed that region in the haploid embryo, based on the haplotype detected in the endosperm sample.

Methods that detect fixed marker sets may be used to determine the genotype of the haploid embryo. To utilize genetic linkage information, high density marker sets for a region are considered when making a genotype determination for any given marker, by comparing observed marker combinations to potential marker combinations to determine parent of origin for a region and/or by using windows to define regions and derive scores based on number of markers that match each parent. Knowing the markers of the origin and haploid inducer parents facilitates determining the genotype of the haploid. There are at most four different haplotypes, one from each of the origin parents and haploid inducer parents) of which at most two can be present in the haploid kernel's endosperm—a total of at most four possible different haplotype combinations. If both HI parents have the same haplotype for given genetic region, a single haplotype is present in the HI line. In this case, there would be only two distinct haplotype combinations possible. Expected marker calls can be determined for all potential haplotype combinations in a given marker set. The haplotype present in the haploid embryo is then determined by comparing the observed marker calls to the potential marker call cases. If the markers of the HI line are not known in advance, they can be determined by examining tissue from the HI line (or from both inbred HI lines if a hybrid HI line is used). If a population of haploid kernels is evaluated where only the origin parents' genotypes are known, it is possible to determine the haplotypes present in the HI parents by evaluating the genotyping calls of the population. If a marker is determined to be homozygous in a haploid endosperm, then the observed allele is present in the haploid embryo. For markers that are homozygous in the haploid endosperm, knowledge of the genotyping results of the HI line is not required to make a determination. By assessing multiple markers, an adequate number of markers may be observed as homozygous in a given region to determine which origin parent the region came from. The remaining markers from that region may then be imputed.

Figure 10:
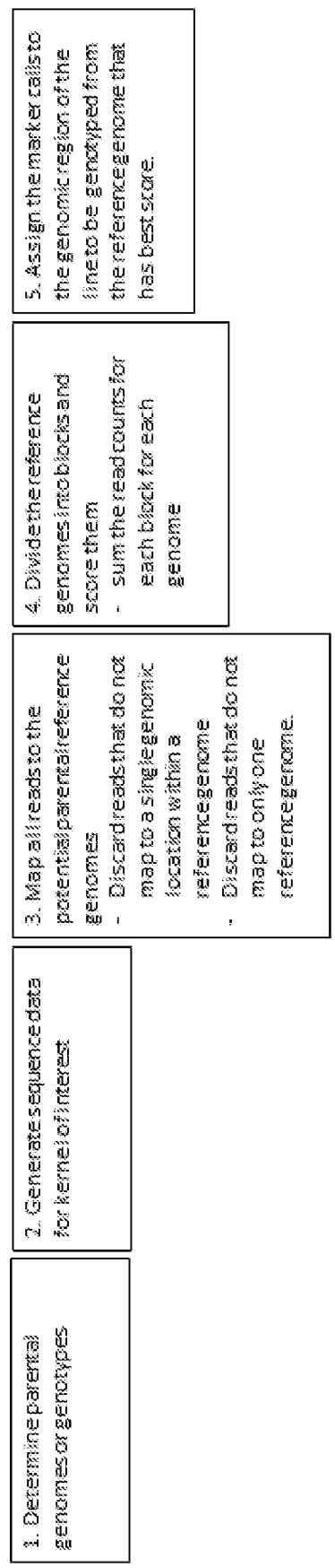
FIG. 10: Shows a schematic for the steps to use when genotyping by low coverage sequencing.

Low-coverage whole genome sequencing methods that detect a stochastic set of markers may also be used to genotype the haploid embryo (FIG. 10). To optimize use of sequence information generated from a haploid kernel, reference genomes of the parents should be available. In many cases, the parents' genomes will not have been fully sequenced and assembled. In those cases, the parental reference genomes may be approximately determined by genotyping, using methods known in the art, and imputing from the genomes of related lines with genome sequences. Alternatively, the parental lines may be sequenced to produce genome information. In cases where many progeny from an origin will be genotyped, the sequence data from individual progeny lines may be pooled or considered together and analyzed to determine the genomes of the parental lines. Even in cases where the parental genomes are genotyped and imputed from known lines, the sequence data from individual progeny lines may be pooled or considered together to confirm or refine the imputed genomes of the parental lines. Also, de novo variation that is present in a parental line can be detected or validated by considering the sequence information of the progeny. Sequencing data may be used to determine which parent a genomic region comes from by comparing the number of sequencing reads that map to a given regions in the parental genomes. By quantifying the number of reads in each region, a score may be generated. In cases where the score for one region is substantially higher than the other, the region in the individual is surmised to be from the higher scoring parental genome and known marker information from the parental genome is assigned to the progeny. Scoring methods may give different weights to sequences of different quality or uniqueness in a genome. Using the methods described herein, there may be up to four different parental genomes to compare against. Since many of the reads will be from the HI line, the HI genome must be considered in generating scores. This can be done by excluding reads or changing relative impact on the scores that sequences have which match the HI line and an origin's genome.

Long molecule sequencing methods that may also be used to genotype the haploid embryo. Because a long DNA read is likely to include many physically linked sequence polymorphisms, it is likely that the molecule can be unambiguously determined to come from one of the potential parental genomes. Additionally, assessment of genetic variation on a long molecule would allow detection of a crossover if the alleles detected during sequencing of the DNA molecule switch from one parent to another at a discrete point. In long molecules, genetic variation other than SNPs and small InDels can be assessed and used to determine the parent of origin of the molecule. For example, the number and arrangement of repeated DNA sequences may be diagnostic of a given parent but this information cannot be easily obtained from many small sequences. Also, SNPs, InDels, or other small changes in repeated sequences can be used to identify the source of a genomic region when in the proper context. For example, a variant of a repeated sequence may be present at hundreds of genomic locations but the presence of that certain variant at a specific location may allow it to be differentiated. Furthermore, very long reads may be used for detecting and using structural variation such as repeat copy number to determine the genotype. Shorter long reads may be used for detecting microhaplotypes.

Example 4: Quantitative Assays for Haploid Embryo Genotyping Using Data from Linked Markers Linked markers tend to transmit together from parents to offspring. Thus, parental haplotypes of linked markers are more likely to be observed in offspring than the haplotypes that are absent in parents. This is true for two linked markers as well as for many linked markers. Moreover, this process can be quantitatively modeled using the linkage relationship among markers, which can be represented by a linkage map.

Quantitative genotyping methods such as multiplex amplicon sequencing can be used to determine the female and/or male allele of the endosperm by evaluating the observed data of multiple amplicon sequence reads based on the expected ratio of 2:1 of an endosperm. With verified pedigree information, parental genotypes will greatly facilitate the determination of the female and/or male allele that the endosperm has. For example, if both parents have the genotype AA, the progeny endosperm will typically have the genotype AA/A. One will generally need more amplicon sequence reads to determine the female and/or male allele of an endosperm with a female (male) parent having a genotype of AT (AT) than the endosperms with a female (male) parent having a genotype of AT (TT). The female alleles of an endosperm are useful in tracing transmission from female parent to haploid kernel only if the female parent is heterozygous.

It is not unusual that a sample has some but insufficient data at a marker to determine the female and/or male allele of the endosperm. Information at linked markers may help to determine the genotype of endosperm of the marker of interest.

TABLE 4

Parental Genotype and sequence reads of endosperm[1,2,3]

| | Origin Genotype | Haploid Inducer Genotypes | Endosperm sequence reads |
|---|---|---|---|
| Marker 1 | A/T | A/T | A3T0 |
| Marker 2 | A/A | A/T | A20T10 |

[1]The recombination fraction between marker 1 and marker 2 is equal to 0.005 (namely, the distance between marker 1 and marker 2 is equal to ~0.5 cM (centiMorgan) apart
[2]Both marker 1 and marker 2 have allele A and T, and X/Y denotes the phased genotype with allele X and Y from its female and male parent, respectively
[3]AxTy denote to having x and y sequence reads with nucleotide A and T at the marker position, respectively For the example described in Table 4, conventional single marker analysis does not generate useful information for the haploid embryo genotype. At marker 1, the reads data of A3T0 (namely 3 and 0 reads with nucleotide A and T at marker position, respectively) is generally considered to be insufficient to call a haploid embryo allele. At marker 2, the haploid embryo allele is expected to be A, which is consistent to the data of sequence reads. However, the haploid embryo allele at marker 2 is uninformative in tracing transmission of the genome from the origin to the haploid embryo.

Useful information can be extracted about the transmission of genomic regions between marker 1 and marker 2, and their vicinity from origin to haploid embryo if data at marker 1 and marker 2 are jointly evaluated. Clearly, the endosperm gets T allele (namely the paternal allele) at marker 2 from its HI inbred. The endosperm gets the paternal allele (namely T) at marker 1 from its HI inbred when there is no recombination between marker 1 and marker 2. Since marker 1 and marker 2 are tightly linked, the probability of having a recombinant event between marker 1 and marker 2 is low (0.5%). If no recombinant event occurs between marker 1 and marker 2, the A allele reads of 3 either come from female parent of the endosperm (namely origin) or are due to noise in the process (such as a mutation(s) or sequencing errors). Given some pre-specified process error, the likelihood of allele of haploid at marker 1 being A or T can be estimated. Assuming reasonably low process noise, the female allele of the endosperm for marker 1, which is identical to the allele of haploid, can be determined to be A.

Use of neighborhood marker information can be extended to multiple markers that are located on either side of the marker, and different types of markers including, but not limited to, SNPs and InDels, can used in the evaluation. In some cases, multiple markers with insufficient data to call genotypes based on their own data can be jointly evaluated to determine their genotypes. More generally, markers that are in linkage disequilibrium defined as having the non-random association of alleles in a given population can be used for this purpose. Also, different statistical and data mining methods including, but not limited to, likelihood based, Bayesian, machine learning, and artificial neuron network based methods.

Example 5: Non-Quantitative Genotyping Methods Used to Determine the Genotype of the Haploid Embryo In this example, haploid kernels were obtained from two different origins but in each case they were harvested from F1 hybrid lines resulting from a haploid induction cross using a hybrid inducer line. The genotypes of both haploid induction parents used to produce the haploid induction line and the genotype of the parents used to produce the F1 individuals that were crossed by the haploid induction line were all previously determined.

A haploid corn kernel from each source was soaked in a low concentration bleach solution for a few hours and then rinsed with water. Using a razor blade, a small piece of endosperm kernel tissue was removed with care taken to not damage the embryo. DNA was extracted from the small piece of endosperm kernel cutting after removal of the pericarp tissue. The remaining kernel was placed on a gel-rite pad, covered by soil and placed in a growth chamber for approximately 6 days. As soon as the seedling emerged a leaf punch was harvested and DNA extracted.

Genotyping from the haploid leaf tissue and endosperm cutting was performed using a maize Infinium® array. Only known SNP markers were considered and classified as homozygous for one or the other allele, heterozygous, or missing.

Two experiments were carried out with similar end results. In each case the total number of SNP markers assessed was similar (a. 24,614 SNP markers; and b. 24,484 SNP markers). Tables 5 and 6 below summarize the results which revealed a high correspondence between the genotypes originating from endosperm and haploid seedling.

TABLE 5

Correspondence between endosperm and haploid seedling genotypes, case #1

| Category of marker | # of markers | Percentage of markers that match genotypes of endosperm and genotype of haploid seedling |
|---|---|---|
| Homozygous in the endosperm | 15,596 | 99.99 |
| Heterozygous in the endosperm | | |
| non-polymorphic in origin | 6,572 | 99.98 |
| non-polymorphic in hybrid | 1,620 | 99.94 |
| haploid inducer remainder | 826 | 98.79 |
| total | 24,614 | 99.95 (5 markers not called) |

TABLE 6

Correspondence between endosperm and haploid seedling genotypes, case #2

| Category of marker | # of markers | Percentage of markers that match genotypes of endosperm and genotype of haploid seedling |
|---|---|---|
| Homozygous in the endosperm | 12,978 | 100% |
| Heterozygous in the endosperm | | |
| non-polymorphic in origin | 9,683 | 100% |
| non-poly morphic in hybrid | 1,252 | 99.84 |
| haploid inducer remainder | 571 | 98.42 |
| total | 24,484 | 99.96 (3 markers not called) |

The invention claimed is:

1. A method of obtaining a doubled haploid plant with a selected genotype, said method comprising the steps of:
 a) obtaining nucleic acids from a plurality of haploid kernels;
 b) assaying said nucleic acids to determine the genotype of the haploid embryo of said kernels, wherein said determining comprises distinguishing the genotype of the haploid embryo from the endosperm genotype of the kernel comprising the haploid embryo;
 c) selecting a kernel having a desired haploid embryo genotype; and
 d) producing a doubled haploid plant from the selected kernel.

2. The method of claim 1, wherein said determining the genotype comprises quantifying the alleles present in the endosperm of a given haploid kernel at a marker locus to determine the allele ratio present in said endosperm.

3. The method of claim 1, wherein one or both of the maternal and paternal parents of said haploid kernels are $F_1$ hybrids.

4. The method of claim 2, wherein said quantifying comprises determining the alleles present at a higher ratio at said marker locus.

5. The method of claim 2, wherein said determining comprises quantifying the alleles present at two or more marker loci.

6. The method of claim 1, further comprising inferring one or more alleles present at one or more markers associated with said genotypes of claim 1.

7. The method of claim 5, wherein said quantifying comprises determining the alleles present at a higher ratio at said marker loci.

8. The method of claim 1, wherein said determining comprises detecting in the endosperm the presence or absence of an allele in the haploid kernel.

9. The method of claim 8, wherein said allele's DNA sequence is present in haploid kernels' origin parent and absent from the haploid inducer parent of the haploid kernels.

10. The method of claim 9, wherein said allele sequence is polymorphic in the origin parent.

11. The method of claim 8, wherein said determining comprises detecting in the endosperm the presence of said at least one allele sequence, wherein the allele sequence is a multiallelic polymorphism.

12. The method of claim 11, wherein the multiallelic polymorphism is selected from the group consisting of single nucleotide polymorphisms (SNPs), insertions or deletions in DNA sequences (InDels), and simple sequence repeats of DNA sequence (SSRs).

13. The method of claim 12, wherein said multiallelic polymorphism comprises a microhaplotype.

14. The method of claim 1, wherein said determining comprises detecting in said endosperm at least one haplotype present in the haploid kernels.

15. The method of claim 1, wherein said determining comprises identifying the nucleotide sequence present in said endosperm.

16. The method of claim 15, wherein said identifying comprises an allele quantification assay.

17. The method of claim 16, wherein the allele quantification assay is quantitative polymerase chain reaction (PCR).

18. The method of claim 15, further comprising comparing said nucleotide sequence to the genomic sequence present in either or both of the parents of the haploid kernels.

19. The method of claim 1, wherein said plurality of haploid kernels comprises at least 50, at least 250, at least 500, or at least 1000 haploid kernels.

* * * * *